Patent Number: 4,503,853
Date of Patent: Mar. 12, 1985

[54] CONTRA ANGLE HANDPIECE FOR DENTAL TREATMENT BY LASER BEAMS

[75] Inventors: Sadayasu Ota, Kyoto; Shinichi Nishimoto, Otsu, both of Japan

[73] Assignee: Kabushiki Kaisha Morita Seisakusho, Kyoto, Japan

[21] Appl. No.: 413,262

[22] Filed: Aug. 31, 1982

[30] Foreign Application Priority Data

Sep. 4, 1981 [JP] Japan .................. 56-132353[U]

[51] Int. Cl.³ .............................................. G02B 5/14
[52] U.S. Cl. ........................... 128/303.1; 122/395; 350/96.2
[58] Field of Search ............... 128/303.1, 395–398; 433/29, 141, 229; 350/96.2

[56] References Cited

U.S. PATENT DOCUMENTS

| | | | |
|---|---|---|---|
| 3,821,510 | 6/1974 | Muncheryan | 128/395 X |
| 4,101,198 | 7/1978 | Heldt | 350/96.2 |
| 4,185,883 | 1/1980 | Chown et al. | 350/96.2 |
| 4,223,978 | 9/1980 | Kummer et al. | 350/96.2 |
| 4,240,695 | 12/1980 | Evans | 350/96.2 X |
| 4,273,535 | 6/1981 | Yamamoto et al. | 433/141 X |
| 4,385,800 | 5/1983 | Basola et al. | 350/96.2 |
| 4,391,487 | 7/1983 | Melman et al. | 350/96.2 |
| 4,421,382 | 12/1983 | Doi et al. | 350/96.2 |

FOREIGN PATENT DOCUMENTS

| | | |
|---|---|---|
| 135443 | 5/1979 Fed. Rep. of Germany | 128/303.1 |
| 2828322 | 1/1980 Fed. Rep. of Germany | 128/303.1 |

*Primary Examiner*—Edward M. Coven
*Attorney, Agent, or Firm*—Koda and Androlia

[57] ABSTRACT

A contra angle handpiece of this invention employs a laser beam transmitting glass fiber for dental treatment in such a manner that the transmission of the beam is carried out not by a reflecting mirror, but by a glass fiber centripetally held with respect to the handpiece by means of resilient grip members. As a result, the disadvantages of the prior art such as reflection factor reduction and reflection angle changes, which result from the use of a reflecting mirror in a contra angle dental handpiece, are eliminated.

3 Claims, 5 Drawing Figures

CONTRA ANGLE HANDPIECE FOR DENTAL TREATMENT BY LASER BEAMS

BACKGROUND OF THE INVENTION

1. Field of the Invention

This invention relates to improvements in a dental handpiece designed to provide dental treatment by irradiating laser beams upon the teeth of a patient.

2. Prior Art

A dental hendpiece designed to provide dental treatment through irradiation of laser beams upon the teeth was previously proposed by the present applicant under the title of the invention "A HANDPIECE FOR DENTAL TREATMENT BY LASER BEAMS" (Japanese Utility Model Application No. 107561/1981). According to the previous application, a contra angle handpiece having a reflecting mirror therein is designed to irradiate the reflected laser beams upon the teeth through a reflection mirror internally provided at the front end of an applicator. Accordingly, the handpiece of the type described is not free from disadvantages in that microdrops of water from the vaporization of saliva on the tooth surface and cinders of India ink applied over the tooth surface before operation, attach to the mirror face gradually reducing reflection efficiency. Furthermore, there is another disadvantage that offers the possibility of the angle of radiation changing by the attached portion of the reflecting mirror becoming loosened in accordance with long term use. Not only is there a problem in connection with continued use, but also there is another disadvantage of reduction in the field of vision in dental treatment caused by the attached portion of the reflecting mirror and an increase in the number of assembling steps.

SUMMARY OF THE INVENTION

In view of the problems and disadvantages of the previous invention proposed by the present applicant, this invention is intended to provide a contra angle handpiece for dental treatment in which no reflecting mirror is used, but instaed a glass fiber curved in accordance with the shape of an applicator is used which is held by a pair of grippers disposed internally in linear positions in the front and rear of the applicator so that the laser beams are irradiated without generation of heat in the direction at right angles with the axis of the handpiece grip unit to enable dental treatment continuously and efficiently in a wide field of vision in treatment and which is low in production cost.

A detailed description will now be given of an embodiment of the invention with reference to the accompanying drawings.

DETAILED DESCRIPTION OF THE INVENTION

Figure 1:
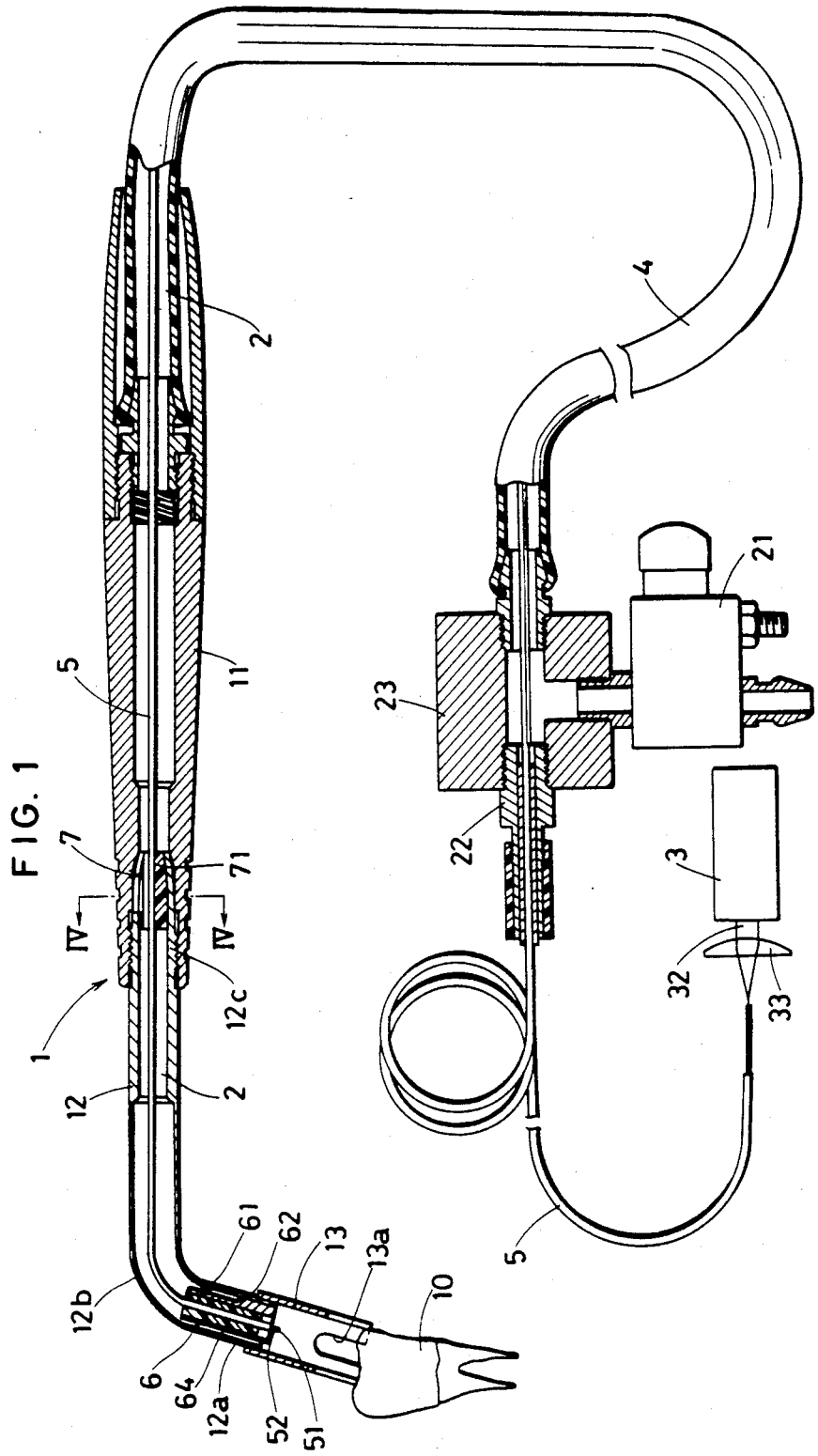
FIG. 1 is a longitudinal sectional view of the essential part of the invention showing the state of use of a handpiece embodying the invention.

FIG. 1 is a longitudinal sectional view showing the state of use of a contra angle handpiece according to the invention. In the figure, the numeral 1 designates a contra angle handpiece which is curved substantially linear on the front side portion of the applicator so as to facilitate the treatment of a tooth 10 such as a molar in the interior of the mouth; 5 designates laser beam transmitting glass fiber; 6 and 7 designate grippers for holding the glass fiber 5 curved along the contra angle applicator 12.

The handpiece 1 comprises a grip unit 11 and a contra angle applicator 12 detachably connected to the grip unit 11. The handpiece 1 contains therein the laser beam transmitting glass fiber 5 in the direction of the major axis of the handpiece and the fiber 5 having the starting end thereof in a laser oscillator 3 is designed to condense by a condensing lens 33 the laser beams 32 oscillated by the oscillator 3 and to send out the beams thus condensed. An ejection source 51 is formed by exposing the core 52 of the fiber 5 at a suitable point of the hollow interior of a laser ejection cylinder 13 connected to the front end of the applicator 12.

Figure 2:
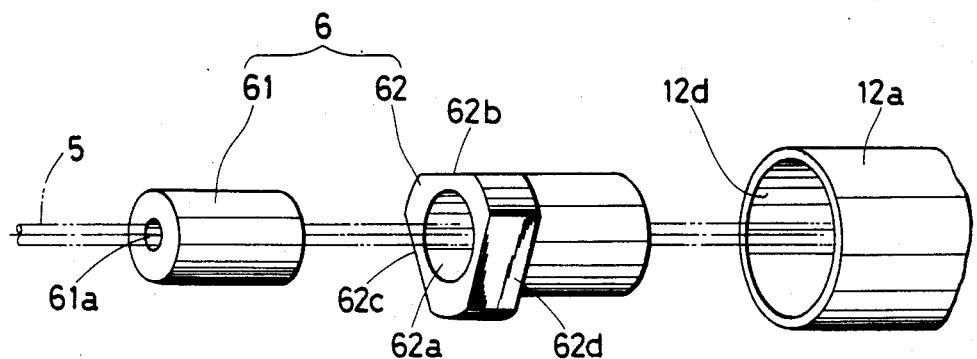
FIG. 2 is an exploded perspective view showing the structure of a resilient gripper in the front portion of the applicator of the handpiece.
Figure 3:
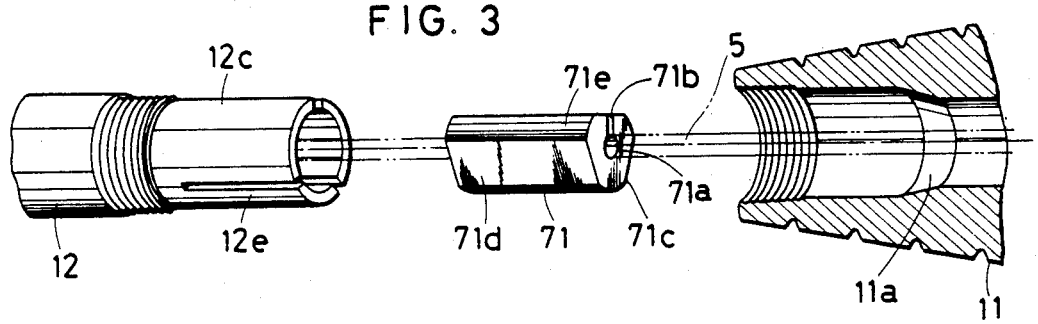
FIG. 3 is an exploded view of the structure of the resilient gripper in the rear portion of the applicator of the handpiece.
Figure 4:
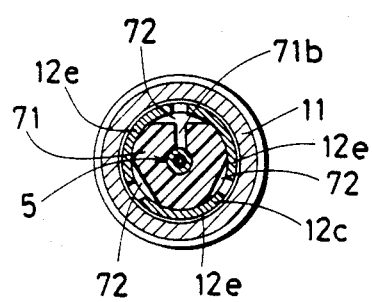
FIG. 4 is a sectional view taken along the line IV—IV of FIG. 1.

The glass fiber 5 is gripped centripetally by a pair of resilient grippers 6 and 7 coaxially incorporated into the applicator 12 in the liner areas 12a and 12c on the front and rear sides of the applicator 12 and is coaxially held in a contra angle portion 12b. The gripper 6 secured to the front portion of the applicator 12 by an adhesive agent comprises a cylindrical elastic supporter 61 and holder 62. As shown in FIG. 2, the supporter 61 is made of silicon rubber which directly grips the glass fiber 5 by a leading hole 61a formed in the center of the supporter 61, and the holder 62 is made of reinforced plastic or die cast aluminum which fits the supporter 61 into an axial hole 62a of the holder 62. When the holder 62 is secured to the front portion of the applicator 12, chamfered portions 62b, 62c and 62d at three portions of the outer circumference of the holder 62 form air passageways 64 between the chamfered portions 62b, 62c and 62d and the inner wall 12d of the applicator 12. The connecting portion between the grip unit 11 and the applicator 12 is constructed so as to permit threaded engagement with each other. The gripper 7 secured to the rear side of the applicator 12 is constructed of a rubber fastener 71 made of silicon rubber clamped centripetally respectively by a tapered hole 11a formed at the front end of the grip unit 11 and backwardly converging and by a collet 12e at the rear end of the applicator 12. This rubber fastener 71 has a split groove 71b for helping insertion of the glass fiber 5 into a leading hole 71a formed in the center of the fastener 71, and the circumferential portion of the fastener 71 has chamfered portions 71c, 71d and 71e adapted to define passageways 72 between the chamfered portions 71c, 71d and 71e and the inner wall of the collet 12e of the applicator 12 when the fastener 71 is clamped by the inner wall of the collet 12e.

In the construction described above, the cylindrical elastic supporter 61 and rubber fastener 71 promote obtuse and smooth curving of the glass fiber 5 at the contra angle portion 12b by their resilient force and prevent the loss of output energy and heat generation o:

the glass fiber due to sudden change in curvature (see FIG. 1). The passageways 72 and 64 are in communication with the air passageway 2 passing through the grip unit 11 and the applicator 12. The air passageway 2, in turn, is in communication with an air passing means, namely, a flexible tube 4 connected with an air feed joint 23 for connecting a three-way changeover electromagnetic valve 21 and glass fiber introduced adapters 22 functions as an air feed passageway for leading the air fed through the three-way changeover electromagnetic valve 21 in the direction of transmission of laser beams and also in time of non-transmission of laser beams forcedly through the handpiece 1 into a laser ejection cylinder 13 connected to the front end of the applicator 12. The residue air pressure in the air passageway 2 and the tube 4 is quickly released into the atmosphere by the three-way changeover electromagnetic valve 21 simultaneously with the starting of the ejection of laser beams and the supply of air from a compressor (not shown) is shut off to completely prevent the ejection of the air during the irradiation of the laser beams.

In the embodiment illustrated, the laser ejection cylinder 13 functions also as a distance spacer between the tooth 10 and the applicator 12 and regulates the amount and strength of irradiation of laser beams ejected from the laser beam ejection source 51. The numeral 13a designates exhaust ports which are provided at four points on the outer circumference of the lower half of the laser ejection cylinder 13 and which are adapted to release the air.

Figure 5:
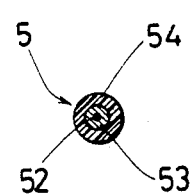
FIG. 5 is an enlarged sectional end view of the glass fibers in their optional position in the embodiment of the invention.

The glass fiber 5 used in the embodiment is further covered with glass fiber. It is demonstrated from experiments that the covered glass fiber functions more effectively in uniformalizing the energy density of transmitting laser beams than the fiber used in the form of a core 52 alone. Since the energy density ejected from the laser oscillator 3 is generally nonuniform, uniformalization of the energy density by the application of multireflection principle in the laser beam transmitting glass fiber 5 constitutes an important factor in providing good dental treatment by irradiating laser beams upon the tooth 10. In this case, glass fiber having a clad layer 53 made of a material which is intermediate in reflection factor between glass fiber and air is more effective in multireflecting property and becomes better in the dispersibility of irradiation mode than a single body of naked fiber core 52, as shown in FIG. 5. Furthermore, it is desirable to cover the clad layer 53 on the outside thereof with an elastic synthetic resin covering 54 of tetrafluoroethylene or polyvinyl chloride, since such materials improve the shape keeping property in the curved portions of the fiber 5. Namely, the fiber having the clad layer 53 formed thereon is desirable in that the resilient force of the fiber at its original state is partly absorbed by elastic deformation of the covering 54. However, even the use of glass fiber core material alone does not depart from the spirit of the invention.

Since the invention is of such a structure as described, the invention has high practical value which makes it possible to perform dental treatment continuously and efficiently with a wide field of vision in treatment by irradiating laser beams in a direction substantially at right angles with the axis of the grip portion of a handpiece without generation of heat by curving the glass fiber in accordance with the curved shape of applicator and using no reflecting mirror and also makes it possible to reduce the cost of production.

We claim:

1. A contra angle handpiece for dental treatment by laser beams comprising a grip unit (11) and a contra angle applicator (12) detachably connected to said grip unit (11), said grip unit (11) and said applicator (12) including therein in a direction of the major axis thereof a laser beam transmitting glass fiber (5) connected to a laser oscillator (3) and being designed to use the terminal end of said glass fiber as an ejection source (15), said handpiece being characterized in that said glass fiber (5) is gripped centripetally by linear areas (12a) and (12c) of front and rear sides of the applicator (12) by a pair of resilient grippers (6) and (7) coaxially contained in said applicator (12), said gripper (6) is secured to the front of and projects out of the applicator and said resilient grippers (6) and (7) comprise a cylindrical elastic supporter (61) and a holder (62) and said gripper (7) is fixed to the connecting portion between the grip unit (11), said glass fiber is smooth-curvedly held in a contra angle portion (12b) and the applicator (12) comprises a tapered hole (11a) at the front end of the grip unit (11) and a rubber fastener (71) clamped by a collet (12e) at the rear end of the applicator (12).

2. A handpiece according to claim 1, wherein a continuous line of an air passageway (2) is formed extending through the interior of said grip unit (11) and said applicator (12) and an air passing means (4) is connected to the rear of said grip unit so as to permit forced introduction of air into said grip unit (11) and said applicator (12) in the direction of laser beam transmission and also in time of no transmission of laser beams.

3. A handpiece according to claim 1, wherein a connecting portion between said grip unit (11) and said applicator (12) is of a threaded structure.

* * * * *